United States Patent
Reina et al.

(10) Patent No.: US 9,560,318 B2
(45) Date of Patent: *Jan. 31, 2017

(54) SYSTEM AND METHOD FOR SURGICAL TELEMENTORING

(71) Applicant: SkySurgery LLC, Coronado, CA (US)

(72) Inventors: G. Anthony Reina, Coronado, CA (US); James Omer L'Esperance, Coronado, CA (US)

(73) Assignee: SKYSURGERY LLC, Coronado, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/875,346

(22) Filed: Oct. 5, 2015

(65) Prior Publication Data
US 2016/0028994 A1    Jan. 28, 2016

Related U.S. Application Data

(63) Continuation of application No. 14/138,045, filed on Dec. 21, 2013, now abandoned.

(Continued)

(51) Int. Cl.
*H04N 7/15* (2006.01)
*G06Q 50/24* (2012.01)
(Continued)

(52) U.S. Cl.
CPC ............ *H04N 7/15* (2013.01); *G06F 19/3418* (2013.01); *G06Q 50/24* (2013.01); *G06T 7/0024* (2013.01);
(Continued)

(58) Field of Classification Search
CPC .......... H04N 7/15; H04N 7/155; G06Q 50/24; G06T 11/00
(Continued)

(56) References Cited

U.S. PATENT DOCUMENTS 4,979,949 A    12/1990  Matsen, III et al.
5,259,042 A *  11/1993  Matsuki ............... H04N 1/4058
                                                358/3.05
(Continued)

FOREIGN PATENT DOCUMENTS

CA    2545508    11/2008

OTHER PUBLICATIONS

US 8,231,638, 07/2012, Swarup et al. (withdrawn)

*Primary Examiner* — Gerald Gauthier
(74) *Attorney, Agent, or Firm* — Procopio, Cory, Hargreaves & Savitch, LLP; Pattric J. Rawlins

(57) ABSTRACT

Apparatus and method for receiving and transmitting streaming live imagery data and audio signals in real time is provided. Imagery data and audio signals are acquired through a telestreamer input device and streamed to one or more remote recipients, allowing remote operators to electronically collaborate by telestrating, annotating, and sketching image overlays. Streaming video images displayed on a monitor are superimposed onto a virtual mesh projected via computer graphics. Vertices of the virtual mesh move according to a computational physics engine. Virtual tools are also superimposed onto a virtual mesh projected via computer graphics. The virtual tools interact with the virtual mesh to deliver real time, realistic modifications of the streaming image data. Recursive positioning of mesh layers and creation of a multi-layered virtual mesh enhance the realistic nature of the modified streaming image data.

9 Claims, 4 Drawing Sheets

Related U.S. Application Data

(60) Provisional application No. 61/745,383, filed on Dec. 21, 2012.

(51) Int. Cl.
| | | |
|---|---|---|
| *G06T 9/00* | (2006.01) | |
| *G06T 7/00* | (2006.01) | |
| *G06T 11/00* | (2006.01) | |
| *G06T 11/60* | (2006.01) | |
| G06F 19/00 | (2011.01) | |
| H04N 19/25 | (2014.01) | |

(52) U.S. Cl.
CPC .............. *G06T 9/001* (2013.01); *G06T 11/00* (2013.01); *G06T 11/60* (2013.01); *H04N 7/155* (2013.01); *G06F 19/321* (2013.01); *G06F 19/3437* (2013.01); *G06T 2207/10016* (2013.01); *H04N 19/25* (2014.11)

(58) Field of Classification Search
USPC ......... 340/572.1; 345/537, 629, 8, 420, 423; 348/14.06, 14.07, 231.5, 14.08, 65, 143; 382/104, 128, 159, 173, 230, 237; 600/410, 600/437, 441; 705/14.54, 3; 709/219; 715/230, 715/753, 756, 716, 863; 250/310; 434/37
See application file for complete search history.

(56) References Cited

U.S. PATENT DOCUMENTS

| | | | |
|---|---|---|---|
| 5,855,583 A | 1/1999 | Wang et al. | |
| 6,016,385 A | 1/2000 | Yee et al. | |
| 6,183,259 B1 | 2/2001 | Macri et al. | |
| 6,259,806 B1 | 7/2001 | Green | |
| 6,393,431 B1 * | 5/2002 | Salvati | A61B 1/00041 |
| 6,445,964 B1 | 9/2002 | White et al. | |
| 6,580,426 B1 | 6/2003 | Small et al. | |
| 6,659,939 B2 | 12/2003 | Moll et al. | |
| 6,664,960 B2 | 12/2003 | Goel et al. | |
| 6,678,764 B2 | 1/2004 | Parvulescu et al. | |
| 6,741,911 B2 | 5/2004 | Simmons | |
| 6,763,176 B1 | 7/2004 | Trottier et al. | |
| 6,795,070 B1 | 9/2004 | Laurent-Chatenet et al. | |
| 6,940,503 B2 | 9/2005 | Vlachos et al. | |
| 7,117,259 B1 | 10/2006 | Rohwer | |
| 7,158,860 B2 | 1/2007 | Wang et al. | |
| 7,240,075 B1 | 7/2007 | Nemirofsky et al. | |
| 7,312,796 B1 * | 12/2007 | Kikinis | G06T 19/00 345/419 |
| 7,372,472 B1 | 5/2008 | Bordeleau et al. | |
| 7,413,565 B2 | 8/2008 | Wang et al. | |
| 7,432,936 B2 | 10/2008 | Woodbury | |
| 7,480,600 B2 | 1/2009 | Massie et al. | |
| 7,492,363 B2 | 2/2009 | Meier et al. | |
| 7,671,249 B2 | 3/2010 | Nishizawa | |
| 7,678,048 B1 * | 3/2010 | Urbano | A61B 8/00 367/103 |
| 7,843,456 B2 | 11/2010 | Xu et al. | |
| 7,860,614 B1 | 12/2010 | Reger | |
| 7,907,166 B2 | 3/2011 | Lamprecht et al. | |
| 7,982,609 B2 * | 7/2011 | Padmanabhan | H04Q 9/00 235/385 |
| 8,035,657 B2 * | 10/2011 | Vau | H04N 1/3871 345/629 |
| 8,073,528 B2 | 12/2011 | Zhao et al. | |
| 8,095,200 B2 | 1/2012 | Quaid, III | |
| 8,105,338 B2 | 1/2012 | Anderson et al. | |
| 8,108,541 B2 | 1/2012 | Shamilian et al. | |
| 8,150,170 B2 * | 4/2012 | Li | G06K 9/622 382/228 |
| 8,169,468 B2 | 5/2012 | Scott et al. | |
| 8,182,476 B2 | 5/2012 | Julian et al. | |
| 8,189,888 B2 | 5/2012 | Takahashi | |
| 8,224,484 B2 | 7/2012 | Swarup et al. | |
| 8,265,342 B2 * | 9/2012 | Connell | G06K 9/00664 340/933 |
| 8,275,202 B2 * | 9/2012 | Kim | G06T 7/0081 382/173 |
| 8,306,399 B1 | 11/2012 | Trottier et al. | |
| 8,582,844 B2 | 11/2013 | Nakayama | |
| 8,610,709 B2 | 12/2013 | Choi et al. | |
| 8,611,988 B2 | 12/2013 | Miyamoto | |
| 8,682,047 B2 * | 3/2014 | Lang | G06K 9/3241 382/128 |
| 8,749,556 B2 | 6/2014 | de Aguiar et al. | |
| 8,768,436 B2 | 7/2014 | Nagao | |
| 8,856,692 B2 * | 10/2014 | Kim | G06F 3/017 715/863 |
| 8,908,766 B2 | 12/2014 | Pace | |
| 8,924,864 B2 * | 12/2014 | Mariotti | G06F 19/321 715/753 |
| 2002/0080094 A1 * | 6/2002 | Biocca | A41D 31/0088 345/8 |
| 2003/0151809 A1 | 8/2003 | Takahashi et al. | |
| 2003/0197720 A1 * | 10/2003 | Moon | G06F 17/30855 715/716 |
| 2004/0039485 A1 | 2/2004 | Niemeyer et al. | |
| 2004/0054760 A1 * | 3/2004 | Ewing | A61B 5/0006 709/219 |
| 2005/0125150 A1 | 6/2005 | Wang et al. | |
| 2006/0022986 A1 * | 2/2006 | LinneVonBerg | G06F 3/14 345/537 |
| 2006/0122482 A1 | 6/2006 | Mariotti et al. | |
| 2007/0144298 A1 | 6/2007 | Miller | |
| 2007/0167702 A1 | 7/2007 | Hasser et al. | |
| 2008/0078030 A1 | 4/2008 | Lee et al. | |
| 2008/0091302 A1 | 4/2008 | Sholev | |
| 2008/0306818 A1 | 12/2008 | Evans et al. | |
| 2009/0012968 A1 | 1/2009 | Hayahi | |
| 2009/0036902 A1 | 2/2009 | DiMaio et al. | |
| 2009/0210801 A1 | 8/2009 | Bakir et al. | |
| 2009/0303316 A1 * | 12/2009 | Iwasaki | A61B 1/00022 348/65 |
| 2009/0326324 A1 | 12/2009 | Munoz-Martinez et al. | |
| 2010/0121655 A1 * | 5/2010 | Lorenz | G06F 19/321 705/3 |
| 2010/0164950 A1 | 7/2010 | Zhao et al. | |
| 2010/0189323 A1 | 7/2010 | Sakagawa | |
| 2010/0245625 A1 * | 9/2010 | Gallagher | G06F 17/30265 348/231.5 |
| 2010/0292706 A1 | 11/2010 | Dutson et al. | |
| 2011/0027761 A1 * | 2/2011 | Nunez | G09B 9/042 434/37 |
| 2011/0107238 A1 * | 5/2011 | Liu | G06Q 10/101 715/756 |
| 2011/0126127 A1 | 5/2011 | Mariotti et al. | |
| 2011/0216167 A1 | 9/2011 | Katz et al. | |
| 2011/0282140 A1 | 11/2011 | Itkowitz et al. | |
| 2011/0282141 A1 | 11/2011 | Itkowitz et al. | |
| 2011/0301616 A1 | 12/2011 | Sanchez et al. | |
| 2012/0071892 A1 | 3/2012 | Itkowitz et al. | |
| 2012/0082371 A1 * | 4/2012 | Bengio | G06K 9/6282 382/159 |
| 2012/0287128 A1 * | 11/2012 | Chang | G06T 17/20 345/423 |
| 2012/0327186 A1 | 12/2012 | Kitamura et al. | |
| 2013/0023730 A1 | 1/2013 | Kitamura et al. | |
| 2013/0141462 A1 | 6/2013 | Niwa et al. | |
| 2013/0184584 A1 * | 7/2013 | Berkey | A61B 8/5292 600/441 |
| 2013/0211230 A1 * | 8/2013 | Sperling | A61B 8/468 600/410 |
| 2013/0284924 A1 * | 10/2013 | Mizuochi | G01N 23/2206 250/310 |
| 2014/0176661 A1 * | 6/2014 | Smurro | G06T 9/001 348/14.06 |
| 2014/0236720 A1 * | 8/2014 | Shunock | G06Q 30/02 705/14.54 |

(56) References Cited

U.S. PATENT DOCUMENTS

| | | | |
|---|---|---|---|
| 2015/0049163 A1* | 2/2015 | Smurro | H04L 65/4015 |
| | | | 348/14.08 |
| 2015/0169525 A1* | 6/2015 | Palm | G06F 17/241 |
| | | | 715/230 |
| 2015/0350552 A1* | 12/2015 | Pryszo | H04N 5/23293 |
| | | | 348/143 |

* cited by examiner

SYSTEM AND METHOD FOR SURGICAL TELEMENTORING

RELATED APPLICATION

The present application is related to U.S. patent application Ser. No. 14/138,045, filed 21 Dec. 2013 and is related to U.S. provisional patent app. No. 61/745,383 filed 21 Dec. 2012, each of which is incorporated herein by reference in its entirety.

BACKGROUND

Field of the Invention

The present invention is generally related to telestration for remote video collaboration with streaming imagery and is more specifically related to enhancing a remote operator's ability to annotate and interact with streaming imagery in a realistic, yet virtualized manner through simulating movement and reaction of the streaming imagery.

Related Art

Industries that develop, manufacturer, and maintain complex products often find an insufficient number of employees with extensive training and experience to meet demand. This is particularly relevant as businesses become more geographically diverse. It is inefficient (and sometime physically impossible) to deploy an expert "into the field" on every occasion at a moment's notice. Rather, companies typically deploy technicians with relative degrees of experience who collaborate with the expert remotely. For example, a multi-national aerospace company might have local technicians in an Italian production plant conferring with senior designers in the United States regarding the fabrication concerns for a specialized airframe. Similarly, technicians on an ocean oil rig may consult with shore side experts to address problems with specialized drilling machinery. Traditionally, video monitoring, as described in previous art, has been instrumental in achieving this collaboration.

Conventional tele-monitoring (aka teleconferencing) allows real-time audio and video tele-collaboration to improve education, training, and performance in many fields. Current collaboration methods include telestration, which can be performed either locally or remotely to identify regions of interest within the video images. For example, television personalities routinely annotate video of live or replayed video broadcasts to highlight their commentary. Similarly, flight engineers can remotely inspect possible damage to space vehicles using telestrated, high-definition images of the equipment while it is still in orbit. In short, expert know-how can be maintained at a centralized location while being mobilized anywhere at a moment's notice.

Current telestration techniques, as defined in prior art, primarily display freehand and other two-dimensional drawings over a video image or series of images. However, true collaboration is better achieved if the remote expert can demonstrate information through movement and manipulation of the images. In this invention, a computer simulation of the objects within the video images is constructed so that they can be manipulated in a more realistic manner.

SUMMARY

The invention relates generally to a collaborative teleconferencing system and method of using the same for generating telestrations and annotations on streaming medical imagery for tele-consultation, tele-collaboration, tele-monitoring, tele-proctoring, and tele-mentoring with others users.

The apparatus includes an image acquisition system adapted for receiving and transmitting medical images, constructed from a computer having communications capability adapted for acquisition and transmission of video signals.

A computer can be defined as typically made of several components such as a main circuit board assembly having a central processing unit, memory storage to store programs and files, other storage devices such as hard drives, and portable memory storage, a power supply, a sound and video circuit board assembly, a display, and an input device such as a keyboard, mouse, stylus pen and the like allowing control of the computer graphics user interface display, where any two or more of such components may be physically integrated or may be separate. Any user on the network can store files on the server and a network server is a computer that manages network traffic.

The present invention improves on existing telestration techniques via the addition of virtual telestration tools that can physically manipulate the video images in a natural way based on a physics model of the object(s) being displayed. Telestration techniques described in prior art rely on freehand drawing of lines or shapes which are then displayed as overlays onto the video images. In the current embodiment, the user controls virtual tools which are able to cut, push, pull, twist, and suture the video images as if they were actually manipulating human tissue.

While the current embodiment is a natural fit for telestrating/telementoring over real-time or stored medical images, such as with surgical telemedicine, the method can be applicable to any telestration requiring one user to demonstrate the use of a tool to an operator who is actually using the tool at that time. Although this technique is naturally suited to such remote student-mentor scenarios, it can also be applied to single-user interfaces. Most notably, with the application of the computational physics model included in the current invention, the user can practice a technique in a virtualized manner on live video images prior to actually performing the maneuver.

This flexibility makes the technique adaptable for the use in remote fieldwork. For example, a telecommunications technician working in a remote location can receive realtime guidance from an expert located elsewhere. Through virtual tool telestration, the expert can annotate which segments to push, pull, twist, and cut in a realistic, but still virtualized manner. The local technician can also use the same annotation tools to practice the task under the guidance of the expert before actually performing the task. By adjusting parameters of the virtual video mesh and computational physics model described below, these annotation techniques can be applied to approximate any objects displayed within the video.

The present invention is accomplished using a combination of both hardware and software. The software used for the present invention is stored on one or more processor readable storage media including hard disk drives, RAM, ROM, optical drives, and other suitable storage devices. In alternative embodiments, some or all of the software may be replaced with dedicated hardware, including custom integrated circuits and electronic processors.

The advantages and novelty of the present invention will appear more clearly from the following description and figures in which the preferred embodiment of the invention is described in detail.

BRIEF DESCRIPTION OF THE DRAWINGS

Description List

Within the figures, the following reference characters are used to refer to the following elements of the exemplary system illustrated in the drawings.
- 10 is an exemplary video stream.
- 12 is a 3D mesh object virtual tool exemplification.
- 14 is a tele-video mesh overlay.
- 16 is an exemplary mesh deformation.
- 18 is an exemplary mesh tear.

FIGURES

Figure 1:
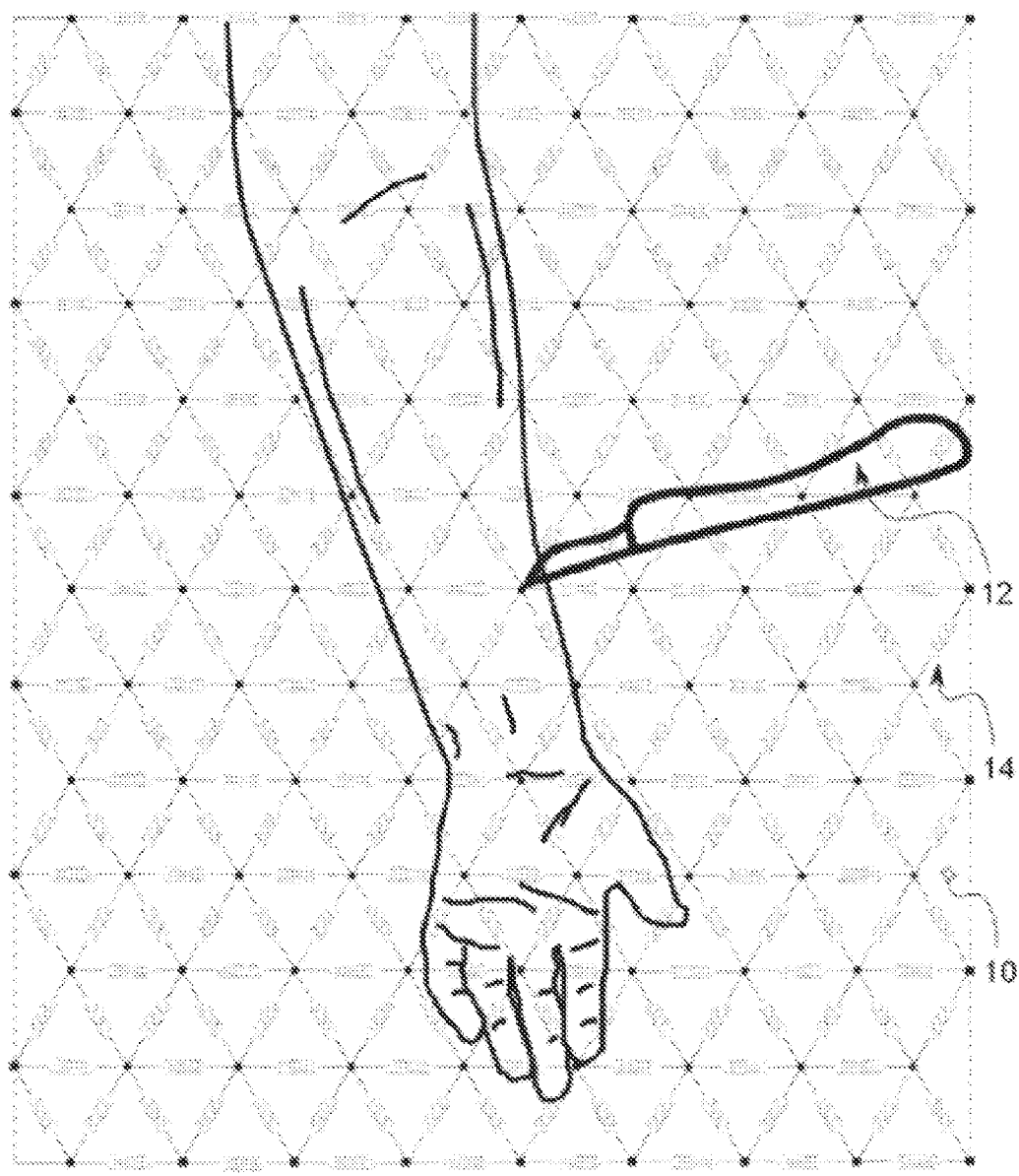

FIG. 1 is a detailed view of the virtual mesh telestration. In this example, a rectangular 12-column grid (14) of equilateral triangles (aka virtual mesh) is constructed via computer graphics. Each vertex (black circle) is connected to another via a computational physics model (spring) which calculates the vertex's three-dimensional position using pre-programmed parameters, including a spring constant, gravitational acceleration, and a damping factor. The border vertices (black squares) remain in fixed positions. The video image of an outstretched left arm (10) is superimposed onto the virtual mesh. A virtual scalpel (12) is superimposed over both 10 and 14.

Figure 2:
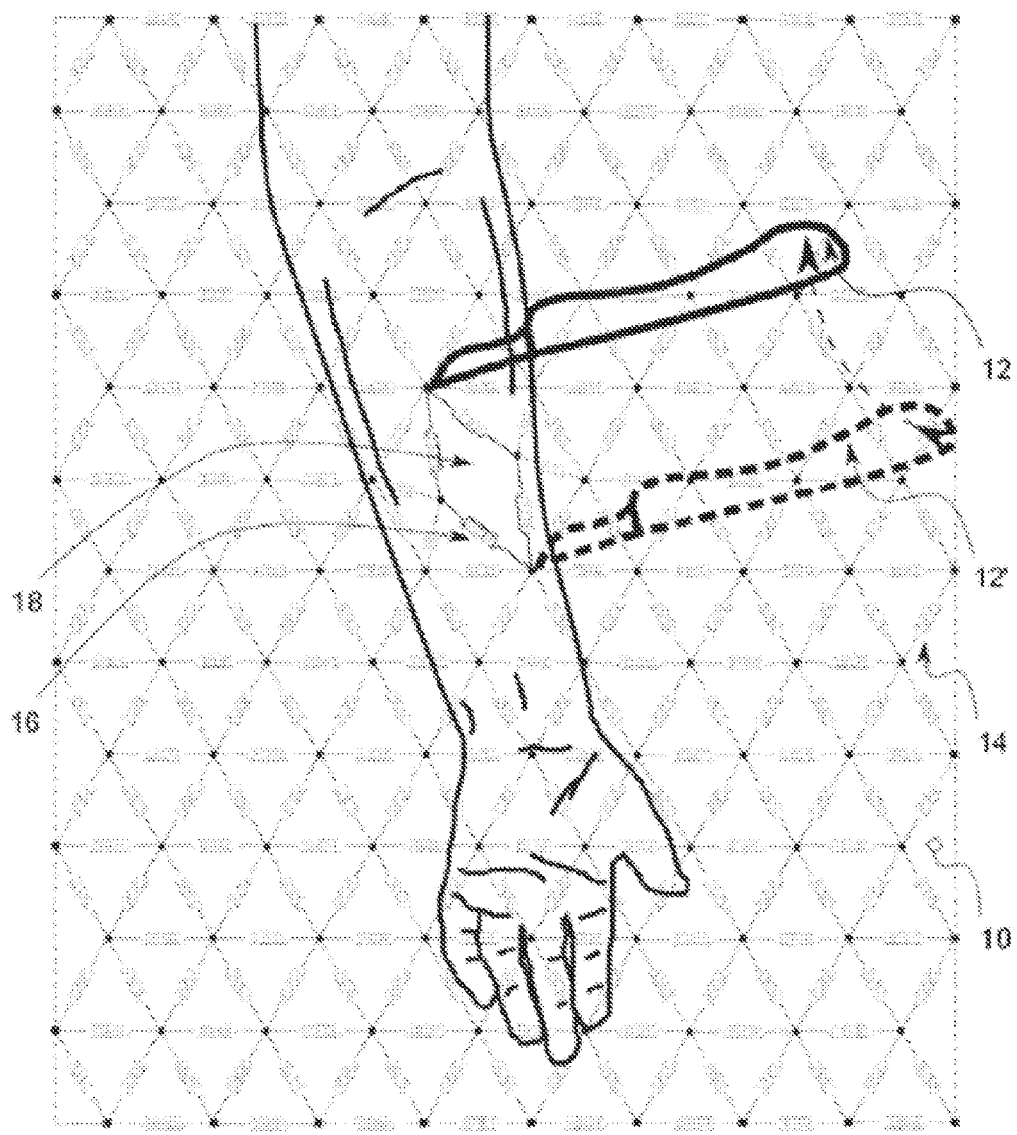

FIG. 2 is a detailed view based on FIG. 1 after the virtual scalpel has been moved to the left which simulates a cut to the virtual mesh (12'→12). The vertices of the virtual mesh (14) move according to the computational physics engine and create new sub-triangles within the mesh (16). This movement creates a void (18) in the mesh. The superimposed video image of the outstretched left arm (10) moves according to the displacement of the associated vertices of the virtual mesh and gives the appearance that the virtual scalpel (12) has in fact "cut" the arm in a realistic manner. Nevertheless, although the original video image is displayed in a distorted manner, the data (and the actual arm) remain unchanged.

Figure 3:
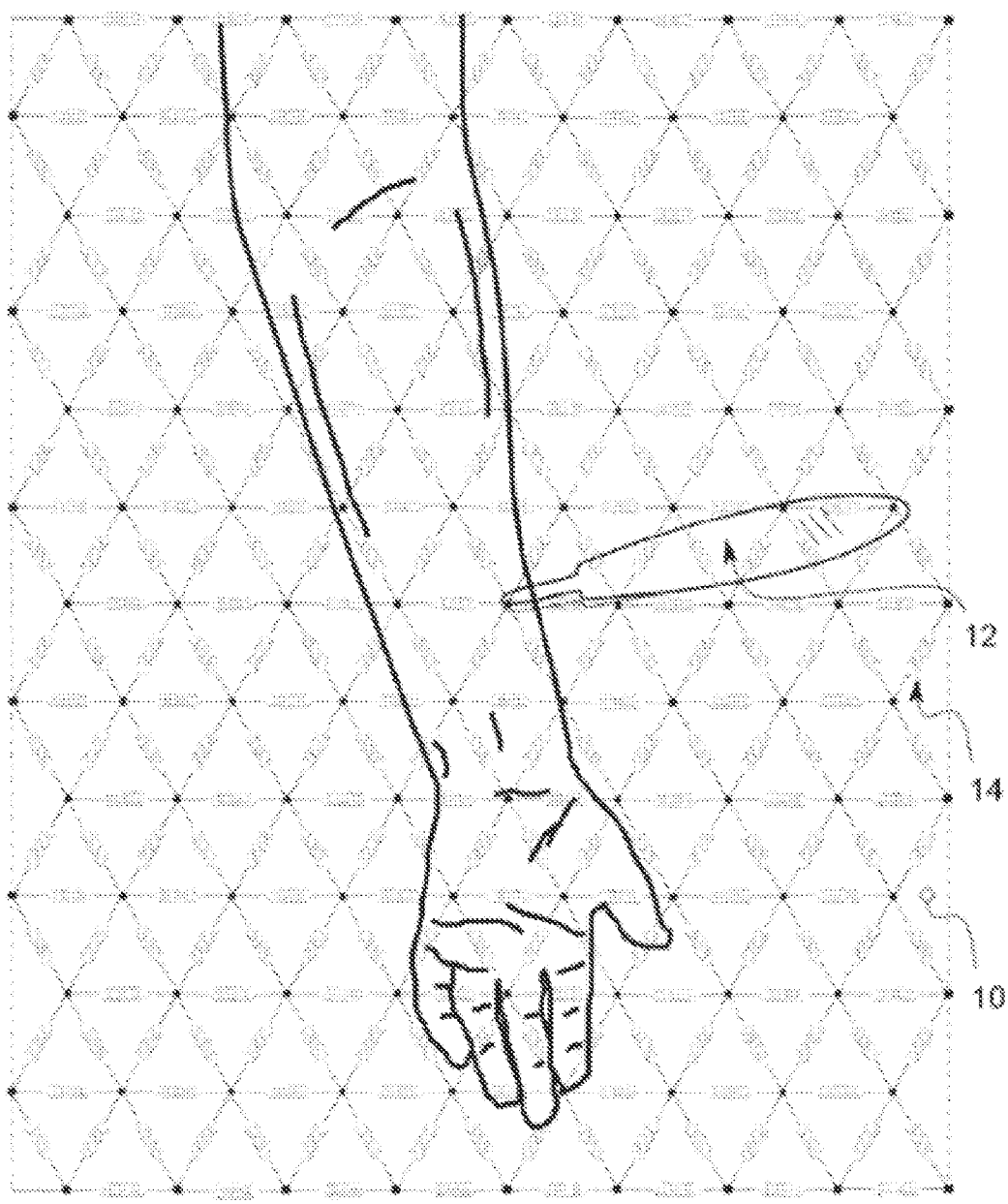

FIG. 3 is a detailed view of the virtual mesh telestration using a forceps tool (12). As with FIG. 1, the virtual mesh is constructed with a 12-column rectangular arrangement of equilateral triangles (14) whose vertices move according to a computational physics model (spring). A video image of an outstretched left arm (10) is superimposed onto the virtual mesh.

Figure 4:
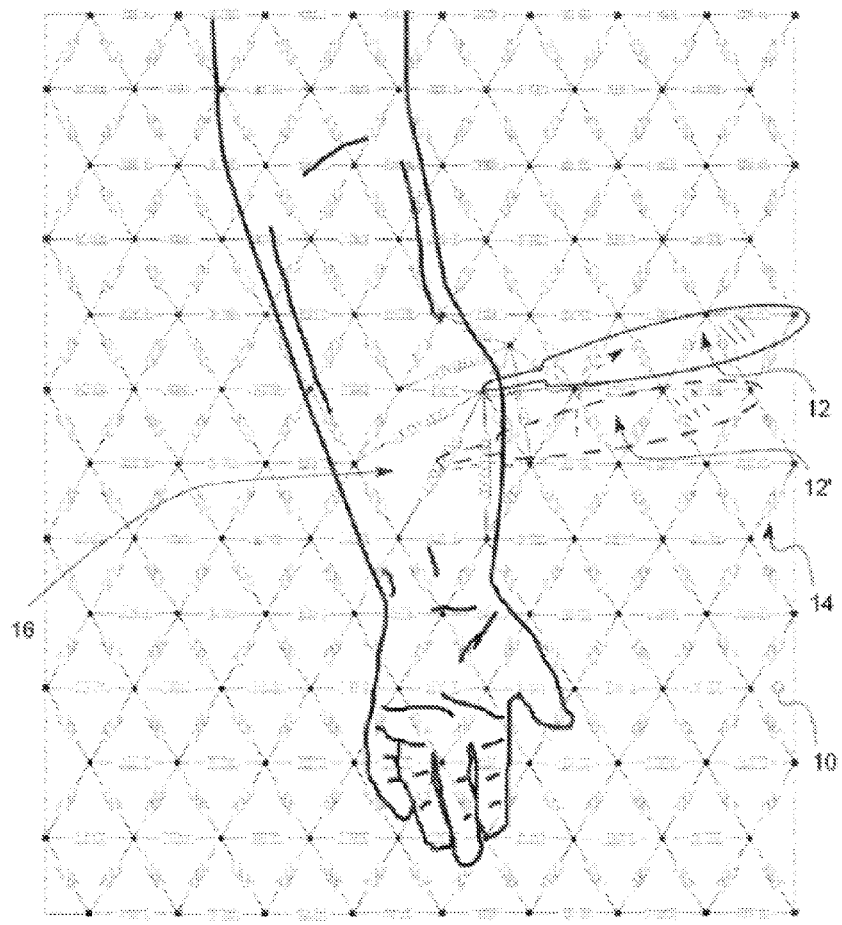

FIG. 4 is a detailed view based on FIG. 3 after the virtual forceps have moved a vertex up and to the left (12'→12). With this tool movement, no vertices are created nor destroyed, but instead move according to the computational physics model (stretched and squeezed springs). The superimposed video image of the outstretched left arm (10) moves according to the displacement of the associated vertices of the virtual mesh and gives the appearance that the virtual forceps has pulled a section of the arm up and to the left. Nevertheless, although the original video image is displayed in a distorted manner, the data (and the arm) remain unchanged.

Figure 5:
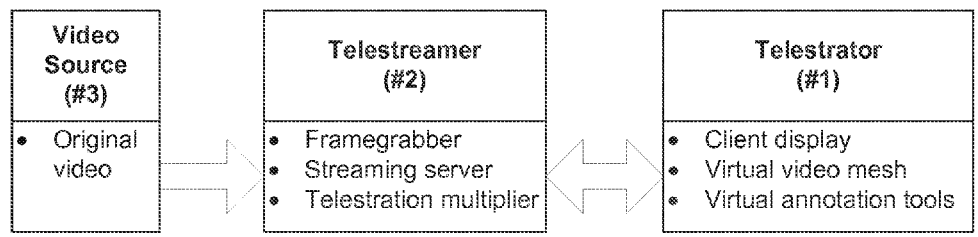

FIG. 5 is a workflow diagram of the application and method. A video source (#3) is captured by a video telestreamer (#2) which digitizes its content and transmits it over telecommunication lines in realtime. A virtual tool telestrator (#1) receives the video telestream and allows the client to annotate the video images using virtual telestration tools. These annotations are streamed back to the telestreamer (#2) which updates the original video source (#1) stream with the annotated version. Note that multiple 3D virtual tool telestrators (#1) may act as clients to the video telestreamer (#2). All clients view the same video images and can annotate them independently.

DETAILED DESCRIPTION

In the following description, a preferred embodiment of the invention is described with regard to process and design elements. However, those skilled in the art would recognize, after reading this application, that alternate embodiments of the invention may be implemented with regard to hardware or software without requiring undue invention.

General Features of the Method and System

There are 3 main components to this method:
(1) the virtual mesh
(2) the UV texture map
(3) the virtual tools.

Virtual Mesh

The virtual mesh is a computer graphics representation of a video display where each vertex of the mesh corresponds to a position within the video image. In a static display, the virtual mesh is analogous to a pixel map of the video image. In this invention, however, the vertices of the virtual mesh are not necessarily aligned with the pixels of the video image. More importantly, the locations of the vertices are not fixed in space, but rather can move with respect to one another as if each vertex were a physical object (or a part of a physical object) in the real world.

In the current instantiation, the virtual mesh is constructed using equilateral triangles arranged in a 12-column grid (FIG. 1). Equilateral triangles were chosen because they are computationally easier to sub-divide than other geometric shapes. Nevertheless, any shape (2D or 3D) can be used to create the mesh. In addition, multiple meshes of varying configurations can be produced to represent features and objects within the streamed imaging modality. Further, the overall mesh is rectangular in shape because video images are usually displayed in this manner; but, the shape of the mesh can changed to conform to the needs of the telestration.

Machine vision techniques may be applied to sub-divide the mesh according to objects within the video image. For example, a mesh displaying a video of an automobile could be sub-divided into body, wheels, and background--with each sub-segment of the mesh being programmed to mimic the physical characteristics of the objects they represent. This would compensate for any relative movement among the camera, objects, or field of view.

In the current embodiment, a surgeon could identify regions of interest within the image (e.g. major organs, nerves, or blood vessels) by encircling them with conventional freehand drawing telestration. An optical flow algorithm, such as the Lucas Kinade method, could be used to track each region of interest within the realtime video. The virtual mesh would be continually updated to change the parameters of the sub-meshes based on the regions of interest. This would ensure, for example, that a cut in the mesh which was made to overlay the prostate would keep the same relative position and orientation with respect to the prostate regardless of movement.

The vertices of the virtual mesh are interconnected in movement using a computational physics model of the object being represented. In the current instantiation, the physics model assumes that vertices are connected via springs which obey the physical constraints of Hooke's Law and gravitational acceleration. By changing the parameters, such as spring constant, gravitational acceleration, and damping factor, the behavior of the virtual mesh can be adjusted between various levels of fluidity. For example, the current embodiment can be made to approximate human skin, but different types of human tissue could also be represented in the same telestrated video.

It should be noted that although the computational physics model is currently formulated to simulate movement in typical environments, it could be equally used to simulate movement of objects in exotic environments, such as in space or underwater by computationally changing the nature of the virtual mesh.

UV Mapping

UV mapping is a three-dimensional (3D) modeling process which maps a two-dimensional (2D) image onto the three-dimensional surface. Other patents and techniques sometimes refer to this technique as "texture mapping". Every 3D object in computer graphics is made up of a series of connected polygons. UV mapping allows these polygons to be painted with a color from a 2D image (or texture). Although in its current instantiation the virtual mesh is a 2D object, it can be texture mapped with a 2D video image in the same manner. Further, using the UV mapping, the same technique can be applied to true 3D virtual meshes of any configuration.

By superimposing the video image onto the virtual mesh using a UV map, the video image will be distorted whenever the virtual mesh is distorted. In effect, the process allows points and segments of the video image to move and react to the telestration. In fact, if polygons within the virtual mesh are deleted (e.g. cutting the mesh as in FIG. 2), the projected video image will not display the area which is mapped to those polygons. Similarly, if the polygon changes shape (e.g. pulling the mesh as in FIG. 4), the projected video image will display the area mapped to that polygon with precisely the same geometric distortion.

Virtual Tools

Virtual tools are computer-generated objects which are programmed to interact with the virtual mesh according to a computational physics engine. In the current instantiation, the invention uses three virtual tools: a virtual scalpel, a virtual forceps, and a virtual suture. All three tools are programmed to push, pull, and twist the virtual mesh according to the physics engine using standard ray-casting techniques and colliders.

The virtual scalpel separates the connections between the triangles that are in contact with the scalpel tip. This results in a void between those triangles and makes the video image appear to have been cut in the mapped area. Further, if an entire section of the virtual mesh is "cut" from the existing mesh, the UV mapped area of the video image will appear to be physically removed from the remainder of the video image. The edge of the cut mesh then acts as an edge of tissue; so the edge of the cut surface will deform when manipulated, independent of the other side of the cut mesh.

The virtual forceps attaches to the triangle closest to the forceps tip when activated. It creates an external force on the attached triangles within the computation physics model of the virtual mesh. The forceps can be used to drag the attached triangles (FIG. 4) and gives the illusion that the video image is being grabbed by the forceps in a realistic manner. After the forceps is deactivated, the external force is removed from the computational physics model. The affected triangles will continue to react to internal (reaction) forces until they eventually return to a steady-state position.

The virtual suture allows the telestrator to add connections between triangles. The suture is modeled by a spring. When activated, the suture tool adds a spring to the computational physics engine between any two points specified. This tool can be used to join previously cut sections of the virtual mesh.

Although in its current instantiation the virtual tools are limited to these three, the flexibility of the computational physics engine allows the technique to be readily expanded to include the use of any tool or object which can be modeled, including drills, retractors, stents, and suction devices.

Application

In order to illustrate the method proposed in this invention, consider the field of surgery. Adequate surgical collaboration requires one practitioner demonstrating a technique to another practitioner. Current telestration techniques are unable to demonstrate surgical techniques, such as dissection, clamping, and suturing. It is not sufficient to know simply where or when to cut; the surgeon must be able to also demonstrate how to cut--how to hold the instrument, how hard to push, and how quickly to move. These limitations of conventional telestration as described in prior art are exacerbated in situations where the practitioners may be in different locations. These telestration techniques are insufficient for true surgical telementoring or any video annotation requiring a procedure to be demonstrated especially when complex techniques are being demonstrated to new students.

Virtual tool telestration, as described herein and which makes up at least a part of the present disclosure, may allow the mentoring surgeon to interact with a virtual video-overlay mesh of the operative field and mimic the technique needed to perform the operation. The surgeon mentor can demonstrate suturing and dissecting techniques while they are virtually overlaid on a video of the actual operative field. Notably, the mentoring surgeon can demonstrate the surgical technique effectively without actually changing the operative field.

Current telestration methods have limited conventional telemedicine to non-surgical fields of medicine. However, with the system and method of the present disclosure, it may be possible that telemedicine/telementoring will become crucial to surgical practice and, indeed, any field where collaboration requires demonstrating rather than merely describing an idea.

In fact, there is growing concern that the advance of minimally invasive surgery (MIS) is grossly outpacing the evolution of surgical training. This application will assist in bridging the learning curves for surgeons performing the MIS procedures. In addition, as live video and other imaging modalities become more prevalent in clinical practice, the telestration described herein will become inherent to all forms of medicine. A virtual tool telestrator is the critical element to enable adequate surgical telestration.

Additionally, telestration is currently used in a number of non-medicine fields. The most common application is with professional sports broadcasting whereby sports commentators can "draw" on the televideo and emphasize certain elements of the video, such as the movement of the players. Adding 3D virtual telestration tools, as described herein, to these existing telestration devices and tools could be invaluable to such modalities. For example, bomb disposal experts could use virtual tools to interact with the remote video signal transmitted by ordinance disposal robots to signal the robot to push or pull certain areas of the field of view. Sculptors could use virtual hands to indicate to their student the proper finger position on a piece of unformed clay--and demonstrate how the clay should move without actually affecting the real world object. Any real world object that can be imaged can be transmitted and manipulated in a collaborative, yet virtualized manner.

Virtual tool telestration may be equally effective in a 2-D or a 3-D environment or representation and differs from what currently exists in the field of telestration. It is typically constructed from two components . 5):
1. a 3D virtual tool telestrator
2. a live video telestreamer These elements may be related to each other in the following exemplary and non-limiting fashion.

The live video telestreamer (#2) may be a computer networking device which allows for audio and video signals to be sent in realtime to remote clients. In one embodiment, the live video telestreamer captures streaming imagery and transmits it over the internet using a real-time streaming protocol (RTSP) in a H.264 video compression/decompression (codec) format.

The virtual tool telestrator (#1) may be a computer program which displays the telestream (#2) as a 3D mesh object on a video monitor, allows for remote users to overlay virtual 3D tools (e.g. forceps, scalpels) which can be moved by the remote user and which can interact with the video mesh. For example, the remote user may virtually grab a section of the video mesh with the forceps and that part of the mesh will move in a manner similar to that of the actual object being displayed in the video (e.g. a section of the bladder neck during prostate removal).

The virtual tool telestrator (#1) will transmit the virtualized surgical telestration of the remote user back to the source live video telestreamer (#2) for display. To conserve transmission bandwidth, the virtual tool telestrator (#1) only sends the position and orientation of the virtual tools and the virtual mesh to the live video telestreamer (#2) along with the timestamp of the current video frame. In this manner, bandwidth requirements and latency are minimized.

The virtual tool telestrator (#1) may be comprised of computer software written, by way of an exemplary and non-limiting example, with mostly open-sourced software development packages, such as by using a programming environment like but not limited to C++, C#, Mono, Silverlight, and Unity3D. The telestrator may include 3D graphics rendering engine, such as but not limited to Unity3D, which may be used to display the 3D virtual tools and a virtual mesh with triangular vertices. The telestrator may also include a physics simulator, such as but not limited to PhysX, to handle the virtual simulation and interaction between the virtualized tools and the video mesh. The telestrator may also include a multimedia player, such as but not limited to AVPro LiveCapture, which may be used to overlay a video input stream onto the virtual mesh to create a virtual operative field. The telestrator will use human input devices, such as the Razer Hydra joystick or the Geomagic Touch to control movement of the virtual tools in a natural way.

A similar computer program exists on the live video telestreamer (#2). However, unlike the virtual tool telestrator (#1), this program renders the graphics without the computational physics engine. Instead, the position and orientation of the virtual tools and virtual mesh that were passed back from the virtual tool telestrator (#1) are used to create an exact rendering of the virtual tool telestration at that timestamp. In this way, the live video telestreamer (#2) can display an exact rendering of the virtual tool telestration to all clients simultaneously.

While the invention has been described with reference to preferred embodiments, it is to be understood that the invention is not intended to be limited to the specific embodiments set forth above. Thus, it is recognized that those skilled in the art will appreciate that certain substitutions, alterations, modifications, and omissions may be made without departing from the spirit or intent of the invention. Accordingly, the foregoing description is meant to be exemplary only, the invention is to be taken as including all reasonable equivalents to the subject matter of the invention, and should not limit the scope of the invention set forth in the following claims.

What is claimed is:

1. A computer implemented method where one or more processors perform steps comprising:
   receiving one or more real time images via a computer network interface, wherein the one or more real time images are aligned to at least one virtual mesh comprising a plurality of vertices and wherein the one or more illustrations are aligned to the virtual mesh;
   storing said one or more real time images in a non-transitory computer readable medium;
   associating one or more illustrations with the one or more real time images;
   aligning the one or more illustrations with the one or more real time images; and
   successively presenting on a display the one or more real time images with the one or more illustrations overlayed on the one or more real time images in accordance with said aligning.

2. The method of claim 1, further comprising:
   moving a first of the one or more vertices of the at least one virtual mesh;
   distorting a portion of the one or more real time images aligned with said first of the one or more vertices of the at least one virtual mesh;
   presenting on the display the distorted portion of the one or more real time images.

3. The method of claim 2, wherein moving a first of the one or more vertices of the at least one virtual mesh is responsive to receiving an instruction to move a first of the one or more illustrations.

4. The method of claim 2, wherein distorting comprises stretching said portion of the one or more real time images.

5. The method of claim 2, wherein distorting comprises compressing said portion of the one or more real time images.

6. The method of claim 2, wherein distorting comprises separating a first section of said portion of the one or more real time images from a second section of said portion of the one or more real time images.

7. The method of claim 6, wherein said separated portion of the one or more real time images appears to be cut when presented on the display.

8. A method comprising:
   projecting video images onto a virtual mesh configured to move according to computational model of an object presented in the video images, wherein the virtual mesh is constructed by computer graphics as a rectangle comprising equilateral triangles having interconnected vertices, and wherein movement between vertices of the virtual mesh is calculated via physics-based calculations; and
   constructing a UV-map to project the video images onto the virtual mesh, wherein the projected video images are transformed as corresponding positions of the vertices of the equilateral triangles in the virtual mesh move based on the physics-based calculations.

9. The method of claim 8, wherein computer-generated, virtual tools are overlaid on the video images and manipulate the images in a realistic manner based on the computational model, wherein said virtual tools comprise three-dimensional renderings of at least one of scissors, sutures, and forceps which can be used to cut, stitch, and manipulate points within the video images and appear to react in a realistic manner in accordance with the virtual tools based on the physics-based calculations.

* * * * *